US00PP33204P2

(12) United States Plant Patent
Ochiai

(10) Patent No.: US PP33,204 P2
(45) Date of Patent: Jun. 29, 2021

(54) ***CLEMATIS* PLANT NAMED 'MANJU'**

(50) Latin Name: ***Clematis* hybrid**
Varietal Denomination: Manju

(71) Applicant: Koichiro Ochiai, Kanagawa (JP)

(72) Inventor: Koichiro Ochiai, Kanagawa (JP)

( * ) Notice: Subject to any disclaimer, the term of this patent is extended or adjusted under 35 U.S.C. 154(b) by 0 days.

(21) Appl. No.: 16/945,207

(22) Filed: Jul. 31, 2020

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./226, 228
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Clematis* plant, 'Manju', characterized by its double flowers that are uniquely shaped with star-shaped outer tepals and a rounded mass of tepaloids in the center, its flowers that are white and greenish white in color, and its floriferous blooming habit with numerous flowers.

2 Drawing Sheets

Botanical classification: *Clematis* hybrid.
Variety denomination: 'Manju'.

CROSS REFERENCE TO A RELATED APPLICATION

This application is related to U.S. Plant Patent for a plant derived from the same breeding program that is entitled *Clematis* Plant Named 'Kokonoe' (U.S. Plant Pat. No. 30,982).

BACKGROUND OF THE INVENTION

The present invention relates to a new and distinct cultivar of *Clematis*, botanically of hybrid origin, and will be referred to hereafter by its cultivar name 'Manju'. 'Manju' is grown as an herbaceous perennial for landscape use or as a terrace potted plant.

'Manju' was derived from a breeding program conducted by the Inventor in Tokyo, Japan. The Inventor made years of crosses between plants of *Clematis florida* (and other species now included in the Florida group of *Clematis*) and plants of *Clematis integrifolia*, and proprietary hybrids between them. The parental plants were unnamed and unpatented. The exact parents are unknown as seeds were pooled from multiple crosses. 'Manju' was selected by the Inventor as a single unique plant from a batch of seedlings in 2000.

Asexual propagation of the new cultivar was first accomplished by softwood stem cuttings by the Inventor in Tokyo, Japan in 2000. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar as grown outdoors. These attributes in combination distinguish 'Manju' as a unique cultivar of *Clematis*.

1. 'Manju' exhibits double flowers that are uniquely shaped with star-shaped outer tepals and a rounded mass of tepaloids in the center.
2. 'Manju' exhibits flowers that are white and greenish white in color.
3. 'Manju' exhibits a floriferous blooming habit with numerous flowers.

'Manju' can be most closely compared to the *Clematis* cultivars 'Kokonoe' and 'Alba Plena' (not patented). 'Kokonoe' is similar to 'Manju' in having full double flowers. 'Kokonoe' differs from 'Manju' in having less flowers that are purple in color and larger in size. 'Alba Plena' is similar to 'Manju' in having flowers that are white in color. 'Alba Plena' differs from 'Manju' in producing less flowers that are larger in size.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listing by Concept Plants, the breeder's representative for licensing (Concept Plants does not sell plants) and Baumschule Hortmann, and Garten Schluter.

BRIEF DESCRIPTION OF THE DRAWINGS

The accompanying colored photographs illustrate the overall appearance and distinct characteristics of the new *Clematis*. The photographs were taken of a 1.5-year-old plant of the new cultivar as grown in a greenhouse in a 12-cm container in Boskoop, The Netherlands.

The photograph in FIG. 1 provides a side view of 'Manju' in bloom.

Figure 1:
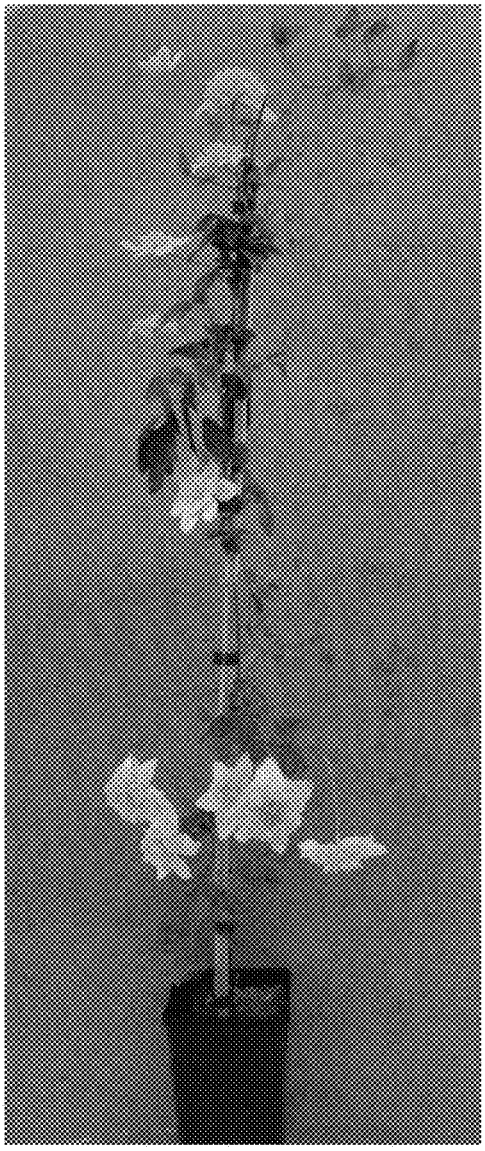
Figure 2:
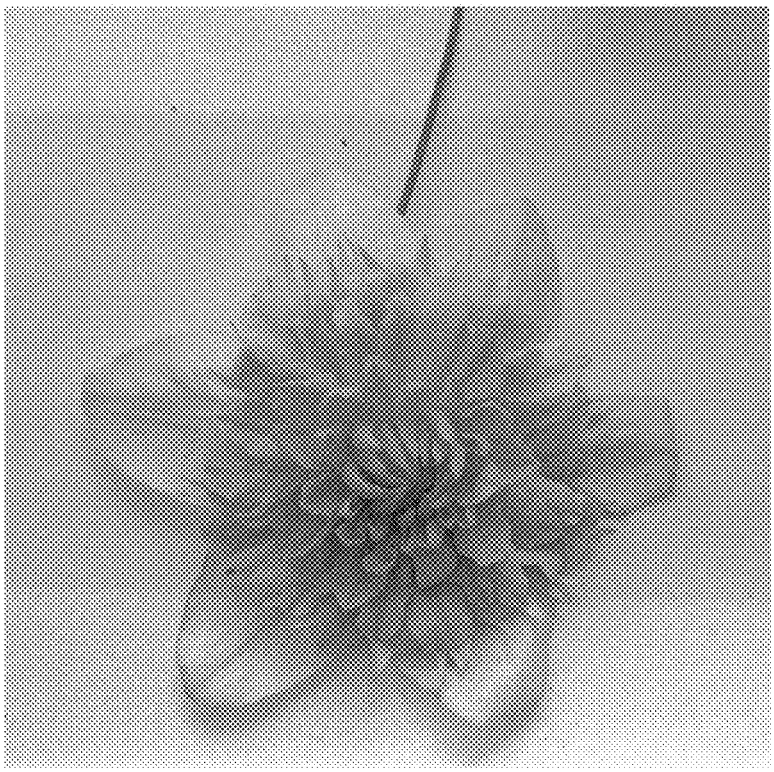
FIG. 2 provides a close-up view of an inflorescence of 'Manju'.
Figure 3:
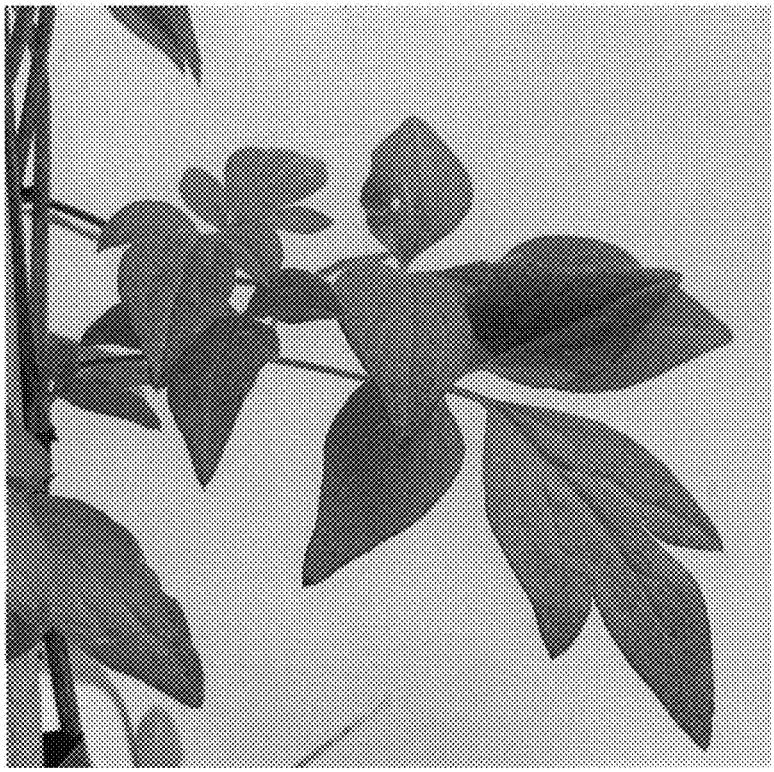
FIG. 3 provides a close-up view of the foliage of 'Manju'.

The colors in the photographs are as close as possible with the digital photography and printing techniques utilized and the color codes in the detailed botanical description accurately describe the new *Clematis*.

DETAILED BOTANICAL DESCRIPTION

The following is a detailed description of 1.5-year-old plants of 'Manju' as grown in a greenhouse in 12-cm containers in Boskoop, The Netherlands. The phenotype of the new cultivar may vary with variations in environmental, climatic, and cultural conditions, as it has not been tested under all possible environmental conditions. The color determination is in accordance with The 2005 Colour Chart of The Royal Horticultural Society, London, England, except where general color terms of ordinary dictionary significance are used.

General description:

*Blooming period*.—Blooms late spring through early autumn in The Netherlands.

*Plant type*.—Deciduous perennial vine.

*Plant habit*.—Climbing with stems emerging from base.

*Height and spread*.—An average of 90 cm in height and 30 cm in width as a 1.5-year-old plant, reaches up to 2.5 m in height in the landscape.

*Cold hardiness*.—At least in U.S.D.A. Zone 6.

*Diseases and pests*.—Have been observed to be healthy with no disease problems however no specific resistance can be identified, no susceptible or resistance to pests has been observed.

*Root description*.—Fleshy, fibrous, and fine, about N167A in color.

*Growth rate*.—Moderate, an average of 10 cm per month in spring.

*Propagation*.—Softwood cuttings from vegetative shoots.

*Root initiation*.—Roots develop in 6 weeks in summer under greenhouse conditions.

*Time required for root development*.—75 to 90 days to develop in a 5-cm container from a 5-cm cutting.

Stem description:

*Shape*.—Round.

*Stem color*.—Young stems 183A, mature stems N199C.

*Stem size*.—Average of 80 cm in length and 2 mm in diameter.

*Stem surface*.—Slightly glossy, stems are sparsely covered with short pubescent hairs.

*Stem aspect*.—Climbing.

*Stem strength*.—Flexible and strong.

*Stem quantity*.—Average of 3.

Foliage description:

*Leaf arrangement*.—Opposite.

*Leaf division*.—Ternate.

*Internode length*.—Ranges between 4 cm and 12 cm.

*Leaf size*.—Up to 7 cm in length and 8 cm in width.

*Leaf quantity*.—Average of 18 (9 pairs) per branch.

*Leaf shape*.—Trifoliate, ovate in outline.

*Leaf fragrance*.—None.

*Leaf attachment*.—Petiolate with leaflets petiolulate.

*Leaf surface*.—Both surfaces are glabrous.

*Leaf size*.—Average of 7 cm in length and 8 cm in width.

*Leaf color*.—Young upper and lower surface; 144A, mature upper surface; 137B and flushed with 166A, mature lower surface; 138B.

*Leaflet shape*.—Lanceolate.

*Leaflet venation*.—Pinnate and slightly reticulate, upper surface color 146D, lower surface color 146C.

*Leaflet margin*.—Primarily entire and occasionally up to 3 crenate teeth.

*Leaflet size*.—Average of 5 cm in length and 3 cm in width.

*Leaflet quantity*.—Average of 3 per leaf.

*Leaflet apex*.—Acute.

*Leaflet base*.—Cuneate.

*Petioles*.—Average of 6 cm in length, 1 mm in diameter, color is 137B to 183A, surfaces are sparsely covered with small pubescent hairs.

*Petiolulates*.—Terminal; average of 2 mm in length, 1 mm in diameter, color is 146B, surfaces are sparsely covered with small pubescent hairs, laterals; 6 mm in length, 1 mm in diameter, color is 137B to 183A surfaces are sparsely covered with small pubescent hairs.

Inflorescence description:

*Inflorescence type*.—Solitary, double.

*Flowering habit*.—Blooms on previous year's growth.

*Flower arrangement*.—Axillary on new shoots in summer.

*Pedicles*.—Average of 11 cm in length and 1.5 mm in diameter, 137B and 183A in color, surface is sparsely covered with pubescent hairs.

*Flower bud description*.—Average of 3.5 cm in length and 1.8 cm in diameter, ovate in shape, 149D with 145C at the base.

*Flower fragrance*.—None.

*Lastingness of the flowers*.—Individual flowers last about 10 days.

*Flower quantity*.—Average of 13 flowers per stem.

*Flower type*.—Fully double, rotate.

*Flower aspect*.—Outward to upright.

*Flower size*.—Average of 8 cm in depth and 2 cm in depth.

*Petals*.—No petals present.

*Sepals*.—No sepals present.

*Tepals*.—Average of 4 to 6, upper surface texture glabrous, matte and velvety, lower surface texture matte and moderately covered with soft short hairs; average of 0.5 mm in length and too small to measure color, rotate in arrangement with multiple rows forming double flowers, un-fused, obovate to oblanceolate in shape, entire margins, acute apex, base cuneate, average of 4 cm in length and 2.3 cm in width, color: when opening upper surface; 149D, with hints of 181A towards the margins, when opening lower surface; 149D with 145C with hints of 181A towards the margins, when mature upper surface; 157B with 149D at the tip, when mature lower surface; 157B and 149B in the center, 155C at the base.

*Tepaloids*.—Average of 150 to 250, upper and lower surfaces are glabrous, arrangement is rotate in multiple rows forming fully double flowers, narrow obovate to oblanceolate in shape, entire margins, base acute, apex acute, average of 2.5 cm in length, 9 mm in width, colors of surfaces match tepals with the tepaloids maturing after the tepals.

Reproductive organs:

*Reproductive organs*.—Flowers are fully double with no reproductive organs present and are fully sterile.

*Seed and fruit*.—No seed or fruit.

It is claimed:

1. A new and distinct cultivar of *Clematis* plant named 'Manju' as herein illustrated and described.

* * * * *